United States Patent
Anneaux et al.

(10) Patent No.: US 9,034,031 B2
(45) Date of Patent: May 19, 2015

(54) PROSTHETIC DEVICE INCLUDING ELECTROSTATICALLY SPUN FIBROUS LAYER AND METHOD FOR MAKING THE SAME

(75) Inventors: Bruce L. Anneaux, Lexington, SC (US); Robert L. Ballard, Orangeburg, SC (US)

(73) Assignee: Zeus Industrial Products, Inc., Orangeburg, NC (US)

(*) Notice: Subject to any disclaimer, the term of this patent is extended or adjusted under 35 U.S.C. 154(b) by 95 days.

(21) Appl. No.: 13/564,927

(22) Filed: Aug. 2, 2012

(65) Prior Publication Data

US 2013/0053948 A1 Feb. 28, 2013

Related U.S. Application Data

(63) Continuation of application No. 12/852,993, filed on Aug. 9, 2010, now Pat. No. 8,262,979.

(60) Provisional application No. 61/232,252, filed on Aug. 7, 2009.

(51) Int. Cl.
*A61F 2/82* (2013.01)
*B29C 47/06* (2006.01)
(Continued)

(52) U.S. Cl.
CPC . *A61F 2/06* (2013.01); *A61L 31/06* (2013.01); *A61L 31/129* (2013.01); *A61L 2400/12* (2013.01); *B82Y 5/00* (2013.01); *D01D 5/003* (2013.01); *D01D 5/0076* (2013.01);
(Continued)

(58) Field of Classification Search
CPC ....... A61F 2/06; A61F 2/82; B01D 2239/025; B01D 2239/0631; B01D 39/1623
USPC ................................. 623/1.11–1.54
See application file for complete search history.

(56) References Cited

U.S. PATENT DOCUMENTS

| | | | |
|---|---|---|---|
| 2,158,416 A | 5/1939 | Formhals | |
| 4,043,331 A | 8/1977 | Martin et al. | |

(Continued)

FOREIGN PATENT DOCUMENTS

| | | | |
|---|---|---|---|
| CN | 101214393 A | 7/2008 | ............. A61L 27/40 |
| EP | 2363516 | 9/2011 | |

(Continued)

OTHER PUBLICATIONS

International Search Report & Written Opinion dated Feb. 25, 2013, for PCT Application No. PCT/US12/056757, filed Sep. 21, 2012.

(Continued)

*Primary Examiner* — David Isabella
*Assistant Examiner* — Ann Schillinger
(74) *Attorney, Agent, or Firm* — Womble Carlyle Sandridge & Rice LLP

(57) ABSTRACT

In accordance with certain embodiments of the present disclosure, a process of forming a prosthetic device is provided. The process includes forming a dispersion of polymeric nanofibers, a fiberizing polymer, and a solvent, the dispersion having a viscosity of at least about 50,000 cPs. A tubular frame is positioned over a tubular polymeric structure. Nanofibers from the dispersion are electrospun onto the tubular frame to form a prosthetic device. The prosthetic device is heated.

37 Claims, 2 Drawing Sheets

(51) Int. Cl.
    *A61F 2/06*       (2013.01)
    *A61L 31/06*      (2006.01)
    *A61L 31/12*      (2006.01)
    *B82Y 5/00*       (2011.01)
    *D01D 5/00*       (2006.01)
    *D01F 6/12*       (2006.01)
    *A61L 27/26*      (2006.01)
    *A61L 27/50*      (2006.01)
    *B01D 39/16*      (2006.01)

(52) U.S. Cl.
    CPC ............... *D01F 6/12* (2013.01); *A61L 27/26* (2013.01); *A61L 27/507* (2013.01); *B01D 39/1623* (2013.01); *B01D 2239/025* (2013.01); *B01D 2239/0631* (2013.01)
    USPC ........................................ 623/1.42; 264/465

(56) References Cited

U.S. PATENT DOCUMENTS

| | | |
|---|---|---|
| 4,044,404 A | 8/1977 | Martin et al. |
| 4,096,227 A | 6/1978 | Gore |
| 4,127,706 A | 11/1978 | Martin et al. |
| 4,143,196 A | 3/1979 | Simm et al. |
| 4,287,139 A | 9/1981 | Guignard |
| 4,323,525 A | 4/1982 | Bornat |
| 4,432,916 A | 2/1984 | Logan |
| 4,552,707 A | 11/1985 | How |
| 4,689,186 A | 8/1987 | Bornat |
| 5,234,739 A | 8/1993 | Tanaru et al. |
| 5,328,946 A | 7/1994 | Tuminello et al. |
| 5,344,297 A | 9/1994 | Hills |
| 5,476,589 A | 12/1995 | Bacino |
| 5,507,770 A | 4/1996 | Turk |
| 5,509,902 A | 4/1996 | Raulerson |
| 5,562,986 A | 10/1996 | Yamamoto et al. |
| 5,665,428 A | 9/1997 | Cha et al. |
| 5,700,572 A | 12/1997 | Klatt et al. |
| 5,702,658 A | 12/1997 | Pellegrin et al. |
| 5,741,333 A | 4/1998 | Frid |
| 5,806,633 A | 9/1998 | Macuga |
| 5,824,046 A | 10/1998 | Smith et al. |
| 5,874,165 A | 2/1999 | Drumheller |
| 5,912,077 A | 6/1999 | Tamaru et al. |
| 5,993,489 A | 11/1999 | Lewis et al. |
| 6,001,125 A * | 12/1999 | Golds et al. ............... 623/23.7 |
| 6,124,523 A | 9/2000 | Banas et al. |
| 6,133,165 A | 10/2000 | Tamaru et al. |
| 6,214,039 B1 | 4/2001 | Banas et al. |
| 6,264,684 B1 | 7/2001 | Banas et al. |
| 6,265,333 B1 | 7/2001 | Dzenis et al. |
| 6,270,523 B1 | 8/2001 | Herweck et al. |
| 6,312,462 B1 | 11/2001 | McDermott et al. |
| 6,383,214 B1 | 5/2002 | Banas et al. |
| 6,402,779 B1 | 6/2002 | Colone et al. |
| 6,416,896 B1 | 7/2002 | Tamaru et al. |
| 6,436,135 B1 | 8/2002 | Goldfarb |
| 6,498,207 B1 | 12/2002 | Hoshikawa et al. |
| 6,505,654 B1 | 1/2003 | Andersen et al. |
| 6,524,334 B1 | 2/2003 | Thompson |
| 6,547,814 B2 | 4/2003 | Edwin et al. |
| 6,579,314 B1 | 6/2003 | Lombardi et al. |
| 6,592,614 B2 | 7/2003 | Lenker et al. |
| 6,641,773 B2 | 11/2003 | Kleinmeyer et al. |
| 6,673,105 B1 | 1/2004 | Chen |
| 6,679,913 B2 | 1/2004 | Homsy |
| 6,699,276 B2 | 3/2004 | Sogard et al. |
| 6,709,455 B1 | 3/2004 | Chouinard |
| 6,740,115 B2 | 5/2004 | Lombardi et al. |
| 6,743,273 B2 | 6/2004 | Chung et al. |
| 6,752,826 B2 | 6/2004 | Holloway et al. |
| 6,770,087 B2 | 8/2004 | Layne et al. |
| 6,790,225 B1 | 9/2004 | Shannon et al. |
| 6,797,217 B2 | 9/2004 | McCrea et al. |
| 6,808,533 B1 | 10/2004 | Goodwin et al. |
| 6,827,737 B2 | 12/2004 | Hill et al. |
| 6,833,153 B1 | 12/2004 | Roorda et al. |
| 6,863,852 B1 | 3/2005 | Ballard et al. |
| 6,899,727 B2 | 5/2005 | Armstrong et al. |
| 6,939,372 B2 | 9/2005 | Dong |
| 6,949,119 B2 | 9/2005 | Myers |
| 6,974,474 B2 | 12/2005 | Pavcnik et al. |
| 7,083,640 B2 | 8/2006 | Lombardi et al. |
| 7,083,697 B2 | 8/2006 | Dao et al. |
| 7,108,912 B2 | 9/2006 | Huang et al. |
| 7,115,220 B2 | 10/2006 | Dubson et al. |
| 7,118,592 B1 | 10/2006 | Dang et al. |
| 7,186,263 B2 | 3/2007 | Golds et al. |
| 7,220,276 B1 | 5/2007 | Williams et al. |
| 7,244,271 B2 | 7/2007 | Lentz et al. |
| 7,244,272 B2 | 7/2007 | Dubson et al. |
| 7,285,132 B2 | 10/2007 | Tseng et al. |
| 7,306,729 B2 | 12/2007 | Bacino et al. |
| 7,316,754 B2 | 1/2008 | Ide et al. |
| 7,354,449 B2 | 4/2008 | Goodwin et al. |
| 7,413,575 B2 | 8/2008 | Phaneuf et al. |
| 7,416,559 B2 | 8/2008 | Shalaby |
| 7,452,371 B2 | 11/2008 | Pavcnik et al. |
| 7,468,071 B2 | 12/2008 | Edwin et al. |
| 7,485,141 B2 | 2/2009 | Marercak et al. |
| 7,510,571 B2 | 3/2009 | Spiridigliozzi et al. |
| 7,520,894 B2 | 4/2009 | Pavcnik et al. |
| 7,524,527 B2 | 4/2009 | Stenzel |
| 7,550,004 B2 | 6/2009 | Bahler et al. |
| 7,560,006 B2 | 7/2009 | Rakos et al. |
| 7,582,240 B2 | 9/2009 | Marin et al. |
| 7,597,710 B2 | 10/2009 | Obermiller |
| 7,641,681 B2 | 1/2010 | Sherry et al. |
| 7,659,219 B2 | 2/2010 | Biran et al. |
| 7,691,141 B2 | 4/2010 | Lewis et al. |
| 7,727,271 B2 | 6/2010 | Kujawski et al. |
| 7,799,261 B2 | 9/2010 | Orr et al. |
| 7,857,608 B2 | 12/2010 | Fabbricante et al. |
| 7,922,761 B2 | 4/2011 | Shalev et al. |
| 7,947,069 B2 | 5/2011 | Sanders |
| 7,981,353 B2 | 7/2011 | Mitchell et al. |
| 8,178,030 B2 | 5/2012 | Anneaux et al. |
| 8,257,640 B2 | 9/2012 | Anneaux et al. |
| 8,262,979 B2 | 9/2012 | Anneaux et al. |
| 8,637,144 B2 | 1/2014 | Ford |
| 8,658,707 B2 | 2/2014 | Xu et al. |
| 8,691,543 B2 | 4/2014 | Gaudette et al. |
| 8,771,582 B2 | 7/2014 | Phaneuf et al. |
| 2001/0000188 A1 | 4/2001 | Lenker et al. |
| 2001/0010012 A1 | 7/2001 | Edwin et al. |
| 2001/0020181 A1 | 9/2001 | Layne |
| 2001/0021870 A1 | 9/2001 | Edwin et al. |
| 2001/0026231 A1 | 10/2001 | Shannon et al. |
| 2001/0032008 A1 | 10/2001 | Wang et al. |
| 2002/0045931 A1 | 4/2002 | Sogard et al. |
| 2002/0111667 A1 | 8/2002 | Girton et al. |
| 2002/0111668 A1 | 8/2002 | Smith |
| 2002/0178570 A1 | 12/2002 | Sogard et al. |
| 2002/0192468 A1 | 12/2002 | Choi |
| 2002/0198588 A1 | 12/2002 | Armstrong et al. |
| 2003/0004559 A1 | 1/2003 | Lentz et al. |
| 2003/0006528 A1 | 1/2003 | Edwin et al. |
| 2003/0040772 A1 | 2/2003 | Hyodoh et al. |
| 2003/0100944 A1 | 5/2003 | Laksin et al. |
| 2003/0114917 A1 | 6/2003 | Holloway et al. |
| 2003/0158598 A1 | 8/2003 | Ashton et al. |
| 2003/0191522 A1 | 10/2003 | Myers |
| 2003/0195611 A1 * | 10/2003 | Greenhalgh et al. ......... 623/1.15 |
| 2003/0204241 A1 | 10/2003 | Dong |
| 2003/0209835 A1 | 11/2003 | Chun et al. |
| 2003/0211135 A1 | 11/2003 | Greenhalgh et al. |
| 2004/0016260 A1 | 1/2004 | Kobayashi et al. |
| 2004/0030377 A1 * | 2/2004 | Dubson et al. ............... 623/1.13 |
| 2004/0033364 A1 | 2/2004 | Spiridigliozzi et al. |
| 2004/0049264 A1 | 3/2004 | Sowinski et al. |
| 2004/0051201 A1 | 3/2004 | Greenhalgh et al. |
| 2004/0054397 A1 | 3/2004 | Smith et al. |
| 2004/0093070 A1 | 5/2004 | Hojeibanet al. |

(56) References Cited

U.S. PATENT DOCUMENTS

| | | |
|---|---|---|
| 2004/0110439 A1 | 6/2004 | Chaikof et al. |
| 2004/0167606 A1 | 8/2004 | Chouinard |
| 2004/0236402 A1 | 11/2004 | Layne et al. |
| 2005/0004653 A1 | 1/2005 | Gerberding et al. |
| 2005/0025974 A1 | 2/2005 | Lennhoff |
| 2005/0113868 A1 | 5/2005 | Devellian |
| 2005/0113909 A1 | 5/2005 | Shannon et al. |
| 2005/0131519 A1 | 6/2005 | Hartley |
| 2005/0137675 A1 | 6/2005 | Dubson et al. |
| 2005/0154448 A1 | 7/2005 | Cully et al. |
| 2005/0187605 A1 | 8/2005 | Greenhalgh et al. |
| 2005/0244453 A1 | 11/2005 | Stucke et al. |
| 2005/0283224 A1 | 12/2005 | King |
| 2005/0288767 A1 | 12/2005 | Kujawski et al. |
| 2006/0015171 A1 | 1/2006 | Armstrong |
| 2006/0020328 A1 | 1/2006 | Tan |
| 2006/0074482 A1 | 4/2006 | Lewis et al. |
| 2006/0200232 A1 | 9/2006 | Phaneuf et al. |
| 2006/0259133 A1 | 11/2006 | Sowinski et al. |
| 2006/0266474 A1 | 11/2006 | Burnside et al. |
| 2007/0026036 A1 | 2/2007 | Falotico et al. |
| 2007/0031607 A1 | 2/2007 | Dubson et al. |
| 2007/0043428 A1 | 2/2007 | Jennings et al. |
| 2007/0087027 A1 | 4/2007 | Greenhalgh et al. |
| 2007/0191936 A1 | 8/2007 | Williams et al. |
| 2007/0207179 A1 | 9/2007 | Andersen et al. |
| 2007/0207186 A1 | 9/2007 | Scanlon et al. |
| 2007/0208410 A1 | 9/2007 | Berra et al. |
| 2007/0244539 A1 | 10/2007 | Lentz et al. |
| 2007/0244569 A1 | 10/2007 | Weber et al. |
| 2007/0276477 A1 | 11/2007 | Lee et al. |
| 2008/0009781 A1 | 1/2008 | Anwar et al. |
| 2008/0021545 A1 | 1/2008 | Reneker et al. |
| 2008/0029617 A1 | 2/2008 | Marshall et al. |
| 2008/0033522 A1 | 2/2008 | Grewe et al. |
| 2008/0119943 A1 | 5/2008 | Armstrong et al. |
| 2008/0143012 A1 | 6/2008 | Norvell et al. |
| 2008/0161907 A1 | 7/2008 | Chen et al. |
| 2008/0167708 A1 | 7/2008 | Molland et al. |
| 2008/0199506 A1 | 8/2008 | Horres et al. |
| 2008/0208323 A1 | 8/2008 | El-Kurdi et al. |
| 2008/0242171 A1 | 10/2008 | Huang et al. |
| 2008/0254091 A1 | 10/2008 | Lee et al. |
| 2008/0261043 A1 | 10/2008 | Greiner et al. |
| 2008/0296805 A1 | 12/2008 | Joo et al. |
| 2008/0319530 A1 | 12/2008 | Leewood et al. |
| 2009/0012607 A1 | 1/2009 | Kim et al. |
| 2009/0018643 A1 | 1/2009 | Hashi et al. |
| 2009/0076587 A1 | 3/2009 | Cully et al. |
| 2009/0088828 A1 | 4/2009 | Shalev et al. |
| 2009/0125092 A1 | 5/2009 | McCrea et al. |
| 2009/0136651 A1 | 5/2009 | Larsen et al. |
| 2009/0157173 A1 | 6/2009 | Bjork et al. |
| 2009/0160099 A1 | 6/2009 | Huang |
| 2009/0163994 A1 | 6/2009 | Quigley et al. |
| 2009/0187240 A1 | 7/2009 | Clerc et al. |
| 2009/0192627 A1 | 7/2009 | Shin et al. |
| 2009/0233057 A1 | 9/2009 | Aksay et al. |
| 2009/0248131 A1 | 10/2009 | Greenan |
| 2009/0258958 A1 | 10/2009 | Ford |
| 2009/0270907 A1 | 10/2009 | Todd et al. |
| 2009/0280325 A1 | 11/2009 | Lozano et al. |
| 2009/0312834 A1 | 12/2009 | Wood et al. |
| 2009/0324680 A1 | 12/2009 | Reneker |
| 2010/0010515 A1 | 1/2010 | Farnsworth et al. |
| 2010/0013126 A1* | 1/2010 | Ishaque et al. ............... 264/465 |
| 2010/0074934 A1 | 3/2010 | Hunter |
| 2010/0093093 A1 | 4/2010 | Leong et al. |
| 2010/0190254 A1 | 7/2010 | Chian et al. |
| 2010/0194000 A1 | 8/2010 | Petras et al. |
| 2010/0248324 A1 | 9/2010 | Xu et al. |
| 2010/0304205 A1 | 12/2010 | Jo et al. |
| 2010/0331965 A1 | 12/2010 | Dugas et al. |
| 2011/0030885 A1 | 2/2011 | Anneaux et al. |
| 2011/0031656 A1 | 2/2011 | Anneaux et al. |
| 2011/0089603 A1 | 4/2011 | Fabbricane et al. |
| 2011/0135806 A1 | 6/2011 | Grewe et al. |
| 2011/0142804 A1 | 6/2011 | Gaudette et al. |
| 2011/0156319 A1 | 6/2011 | Kurokawa et al. |
| 2012/0114722 A1 | 5/2012 | Ballard et al. |
| 2013/0085565 A1 | 4/2013 | Eller et al. |
| 2013/0184808 A1 | 7/2013 | Hall et al. |
| 2013/0184810 A1 | 7/2013 | Hall et al. |
| 2013/0189464 A1 | 7/2013 | Ford |
| 2014/0067047 A1 | 3/2014 | Eller et al. |
| 2014/0072694 A1 | 3/2014 | Hall et al. |
| 2014/0074225 A1 | 3/2014 | Hall et al. |
| 2014/0079758 A1 | 3/2014 | Hall et al. |
| 2014/0081414 A1 | 3/2014 | Hall et al. |
| 2014/0086971 A1 | 3/2014 | Hall et al. |
| 2014/0248418 A1 | 9/2014 | Eller et al. |
| 2014/0249619 A1 | 9/2014 | Eller et al. |
| 2014/0273703 A1 | 9/2014 | Mower et al. |

FOREIGN PATENT DOCUMENTS

| | | | |
|---|---|---|---|
| GB | 2015118 | 9/1979 | |
| JP | 02-0571379 | 10/1996 | |
| JP | 2006-326579 | 12/2006 | |
| JP | 2007-224466 | 9/2007 | |
| KR | 10-0820162 | 4/2008 | |
| KR | 10-0845239 | 7/2008 | |
| WO | WO 98/00090 | 1/1998 | ............... A61J 2/06 |
| WO | WO 98/31306 | 7/1998 | |
| WO | WO 2005/018600 | 3/2005 | |
| WO | WO 2005/055834 A1 | 6/2005 | ............ A61B 17/00 |
| WO | WO 2005/060875 | 7/2005 | |
| WO | WO 2008/022993 | 2/2008 | |
| WO | WO 2008/109116 | 9/2008 | |
| WO | WO 2009/127170 | 10/2009 | |
| WO | WO 2010132636 | 11/2010 | |
| WO | WO 2011-056154 | 5/2011 | |
| WO | WO 2012/103501 | 8/2012 | |
| WO | WO 2013/109528 | 7/2013 | |
| WO | WO 2014/007979 | 1/2014 | |
| WO | WO 2014/047065 | 3/2014 | |
| WO | WO 2014/047379 | 3/2014 | |

OTHER PUBLICATIONS

International Search Report and Written Opinion dated May 23, 2012 for PCT/US2012/023006.
Preparation of polytetrafluoroethylene ultrafine fiber mats with electrospinning process; Sijun et al.; Materials Science Forum vols. 675-677 (2011); pp. 827-830.
U.S. Appl. No. 13/787,327, filed Mar. 6, 2013, Hall et al.
U.S. Appl. No. 13/826,618, filed Mar. 14, 2013, Hall et al.
U.S. Appl. No. 13/827,775, filed Mar. 14, 2013, Lampropoulos et al.
U.S. Appl. No. 13/829,452, filed Mar. 14, 2013, Hall et al.
Kim et al., "Structural Studies of Electrospun Cellulose Nanofibers," *Polymer*, 2006, pp. 5097-5107, vol. 47.
PCT International Search Report from PCT/US10/024246, dated Aug. 16, 2010.
Written Opinion of the International Searching Authority, PCT/US10/024246, dated Aug. 16, 2010.
International Search Report (PCT/US2010/044874)—2 pages. (ZEUS-1-PCT).
International Search Report (PCT/US2010/044879)—2 pages. (ZEUS-1-PCT).
PCT Written Opinion from International Application No. PCT/US2010/044874, filed Aug. 9, 2010 (8 pages).
PCT Written Opinion from International Application No. PCT/US2010/044879, filed Aug. 9, 2010 (6 pages).
International Search Report and Written Opinion dated Jul. 18, 2013 for PCT/US2013/032771.
Office Action issued on Jan. 2, 2014, for co-pending Chinese patent application No. 201080034893.1 (including translation of text portion).
Electrospinning of cyclodextrin functionalized polyethylene oxide (PEO) nanofibers; European Polymer Journal, Pergamon Press Ltd., Oxford, GB, vol. 45, No. 4, Dec. 25, 2008, pp. 1032-1037.

(56) References Cited

OTHER PUBLICATIONS

Supplementary Partial European Search Report from co-pending European patent application 10807285.1, dated Aug. 19, 2013.
Supplementary Partial European Search Report from co-pending European patent application 10807287.7, dated Aug. 19, 2013.
Office Action issued on Dec. 30, 2013, for co-pending Chinese patent application No. 201080034892.7 (including translation of text portion).
Office Action issued on Jan. 9, 2014, for co-pending Japanese patent application No. 2012-523995 (including translation of text portion).
Response to Aug. 29, 2014 Non-Final Office Action, filed with USPTO on Nov. 25, 2014, from U.S. Appl. No. 14/152,590, filed Jan. 10, 2014.
Office Action dated May 9, 2014 from U.S. Appl. No. 13/360,444, filed Jan. 27, 2012.
Response to May 9, 2014 Office Action filed Aug. 11, 2014 from U.S. Appl. No. 13/360,444, filed Jan. 27, 2012.
Office Action dated Jul. 2, 2014 from U.S. Appl. No. 14/044,050, filed Oct. 02, 2013.
Office Action dated Aug. 29, 2014 from U.S. Appl. No. 14/152,590, filed Jan. 10, 2014.
Office Action dated Mar. 3, 2014 from U.S. Appl. No. 13/742,025, filed Jan. 15, 2013.
Response to Mar. 3, 2014 Office Action filed Jun. 19, 2014 from U.S. Appl. No. 13/742,025, filed Jan. 15, 2013.
Office Action dated Sep. 22, 2014 from U.S. Appl. No. 13/787,327, filed Mar. 6, 2013.
U.S. Office Action dated Oct. 10, 2014, from U.S. Appl. No. 13/742,025, filed Jan. 15, 2013.
Role of chain entanglements on fiber formation during electrospinning of polymer solutions: good solvent, non-specific polymer-polymer interaction limit—Shenoy et al.—Science Direct (2005)—pp. 3372-3384.
European Search Report dated Aug. 19, 2014 for EP12755426.9.
Office Action dated Dec. 25, 2014, from co-pending Japanese patent application No. 2014-000814.
U.S. Office Action dated Feb. 4, 2015, for U.S. Appl. No. 13/360,444, filed Jan. 27, 2012.
International Preliminary Report on Patentability for PCT Application No. PCT/US2012/023006, filed Jan. 27, 2012.
International Search Report for PCT Application No. PCT/US2012/023006, filed Jan. 27, 2012.
Office Action dated Mar. 18, 2015, from corresponding U.S. Appl. No. 13/564,925.
Office Action dated Mar. 13, 2015, from corresponding U.S. Appl. No. 14/331,375.

* cited by examiner

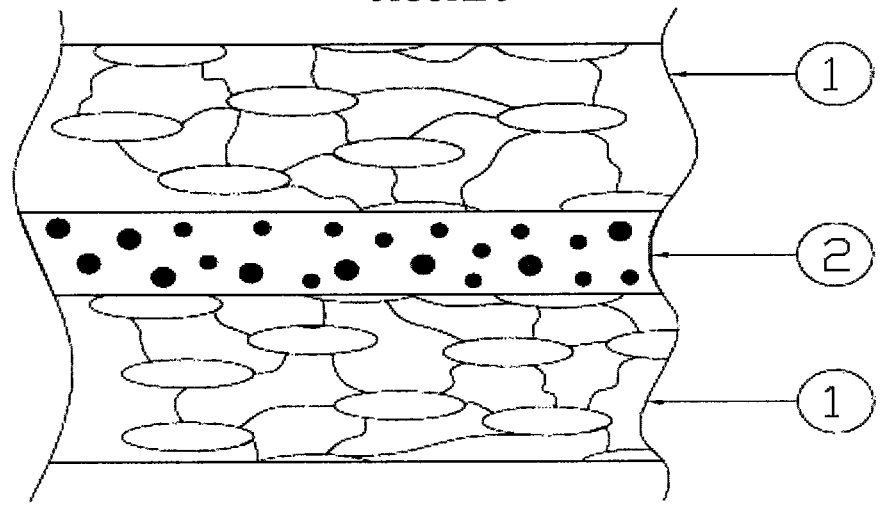
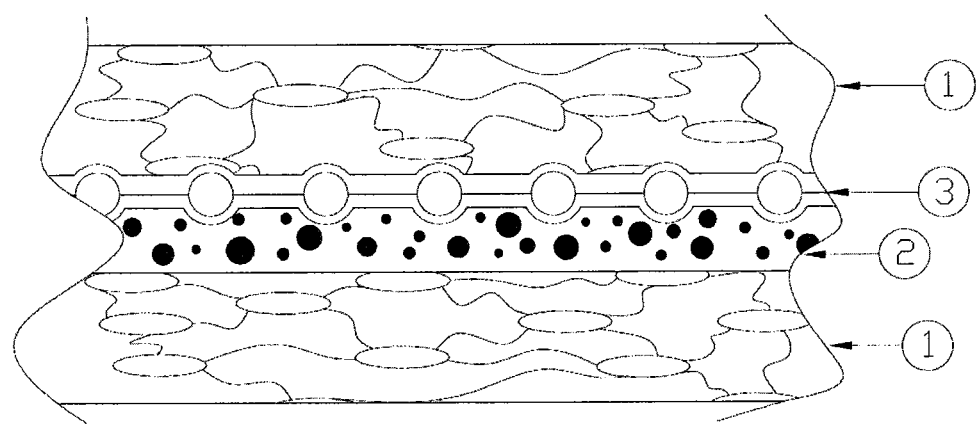

PROSTHETIC DEVICE INCLUDING ELECTROSTATICALLY SPUN FIBROUS LAYER AND METHOD FOR MAKING THE SAME

CROSS-REFERENCE TO RELATED APPLICATION

The present application is a continuation application of U.S. application Ser. No. 12/852,993 filed on Aug. 9, 2010 now U.S. Pat. No. 8,262,979 which is based on and claims priority to U.S. Provisional Application 61/232,252 having a filing date of Aug. 7, 2009, which is incorporated by reference herein.

BACKGROUND

The successful use of extruded tubes of expanded polytetrafluoroethylene (ePTFE) as a synthetic implantable vascular prostheses or tubular graft, designed in particular for the application of synthetic vascular prosthesis or tubular grafts is well known and documented. ePTFE, validated through significant clinical studies, is particularly suitable as a vascular prosthesis or tubular graft as it exhibits superior bio-compatibility and can be mechanically manipulated to form a well defined porous microstructure known to promote endothelialization. PTFE has proven to exhibit a low thrombogenic response in vascular applications. When seeded or infused with a cardio protective agent, the microporous structure, formed anodes and fibrils, allows natural tissue ingrowth and cell endothelialization when implanted in the vascular system. This contributes to long term healing and patency of the tubular graft.

In the prior art, U.S. Pat. No. 6,436,135 Goldfarb, the microstructure of a synthetic vascular prostheses or tubular graft formed of ePTFE is categorized by a fibrous state which is further defined by irregularly spaced nodes interconnected by elongated fibrils or microfibers. The method and techniques for creating this structure have been known for more than three decades and is, in fact, quite simple to one skilled in the art. The distance between the node surfaces that is spanned by the fibrils is defined as the inter-nodal distance (IND). A tubular graft having a specific range of IND enhances tissue ingrowth and cell endothelialization as the tubular graft is inherently porous. The IND range is also small enough to prevent transmural blood flow and thrombosis but not less than the maximum dimension of the average red blood cell, between 6μ and 80μ.

The prior art is filled with examples of microporous ePTFE tubular vascular prosthesis or tubular grafts. The porosity of an ePTFE vascular prosthesis or tubular graft is controlled by the mechanical formation of the IND or the microporous structure of the tube. IND with the defined structure referenced produces results of tissue ingrowth as well as cell endothelialization along the inner and outer surface of the vascular prosthesis or tubular graft.

Similarly, stents are commonly used to restore and maintain body passages, such as blood vessels. Often, biocompatible materials, including grafts, can be provided on the inner or outer surfaces of the stent to reduce reactions associated with contact of the stent with the body.

However, it is difficult with such conventional devices to manipulate mechanical properties, cellular proliferation, cellular permeability, fluid permeability, adhesion to a structural frame, and/or incorporation of an active therapeutic component in the same. Further, such conventional devices do not allow for coating of complex geometries that otherwise could not be covered with ePTFE or other materials alone.

Thus, a need exists for processes that address the deficiencies described above. Prosthetic devices made from such processes would also be particularly beneficial.

SUMMARY

In accordance with certain embodiments of the present disclosure, a process of forming a prosthetic device is provided. The process includes forming a dispersion of polymeric nanofibers, a fiberizing polymer, and a solvent, the dispersion having a viscosity of at least about 50,000 cPs. A tubular frame, such as a stent, is positioned over a tubular polymeric structure. Nanofibers from the dispersion are electrospun onto the tubular frame to form a prosthetic device. The prosthetic device is heated.

In other embodiments of the present disclosure, a process for forming a prosthetic device includes forming a dispersion of polymeric nanofibers, a fiberizing polymer, and a solvent, the dispersion having a viscosity of at least about 50,000 cPs. Nanofibers from the dispersion are electrospun onto a tubular polymeric structure. A layer of polymeric material is wrapped over the nanofibers and around the tubular polymeric structure to form a prosthetic device. The composite structure is heated.

In still other embodiments of the present disclosure, a process of forming a prosthetic device is disclosed. The process includes forming a dispersion of polymeric nanofibers, a fiberizing polymer, and a solvent, the dispersion having a viscosity of at least about 50,000 cPs. A tubular frame is positioned over a tubular polymeric structure. Nanofibers from the dispersion are electrospun onto the tubular frame. A layer of polymeric material is wrapped over the nanofibers and around the tubular frame and tubular polymeric structure to form a prosthetic device. The prosthetic device is heated.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figures in which:

FIGS. 1-4 illustrate cross-sectional views of different prosthetic devices in accordance with the present disclosure.

DETAILED DESCRIPTION

Figure 1:
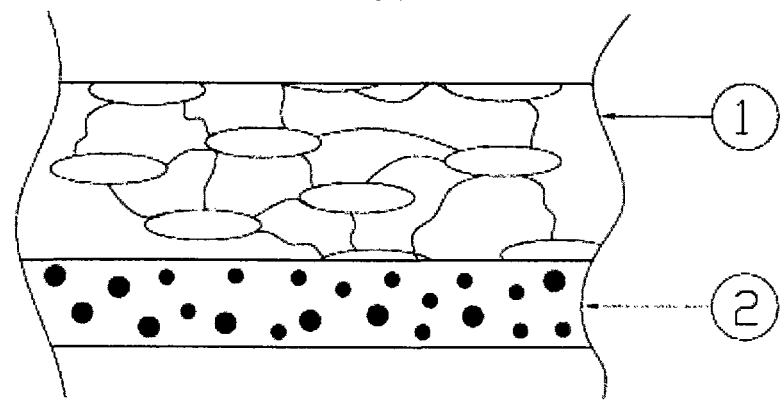

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

The present invention is related to tubular prosthetic devices (also referred to herein as "tubular vascular prostheses" and/or "tubular grafts" and/or "tubular frames") comprising electrospun (also referred to herein as "espin" and/or "espun" and/or "espinning") fibers around a central lumen of such devices. In certain embodiments, the central lumen can include expanded polytetrafluoroethylene (also referred to herein as "ePTFE"). In certain embodiments, the espin fibers can include polytetrafluoroethylene (also referred to herein as "espin PTFE"), however, many other suitable materials can be espun and used in addition to or in combination with such espin PTFE. For example, other suitable materials that can be espun in accordance with the present disclosure include nylons, polyurethanes (PU), polyesters, fluorinated ethylene propylene (FEP), or the like. Polymers that can be placed in a solution have the potential to be espun. Polymer particles that can be made into dispersions (such as, PTFE, FEP, and the like) also have the potential to be espun. The dispersions (espun PTFE) must be sintered to develop the desired properties, but many polymers espun from solution develop their properties during spinning and drying. The attachment of the espin layer(s) can occur during sintering.

In certain embodiments of the present disclosure, an implantable microporous tubular vascular prosthesis or tubular graft comprised primarily of micron and sub-micron sized electrostatically spun PTFE fibers in a random orientation around a central lumen is described. The tubular vascular prosthesis or tubular graft may include one or more layers forming a composite structure of electrostatically spun PTFE fibers around a tubular structure such as a tubular vascular prosthesis, tubular graft, tubular frame, or combinations thereof.

The present disclosure offers a number of advantages over conventional processes and devices including: 1) the ability to incorporate layers with vastly different pore structures and sizes, these different structural layers can be used to manipulate mechanical properties, cellular proliferation, cellular permeability, fluid permeability, adhesion to a structural frame, and/or incorporation of an active therapeutic component; 2) the ability to make a composite construction with vastly different components enabling a broader range of therapeutic uses and structures; 3) improved bonding of PTFE layers to structural frames and to other layers of the construct; 4) the ability to incorporate an espin layer that closely mimics that of the extracellular matrix affording greater control of cellular response; and 5) enabling the coating of complex geometries that otherwise could not be covered with ePTFE or other materials alone.

The tubular structure can include a self sealing thermoplastic or elastomeric component, as described above, as well as a selection of bioactive agents. Examples of such bioactive agents that can be utilized in connection with the devices of the present disclosure include but are not limited to antibiotics, antifungals and antivirals such as erythromycin, tetracycline, aminoglycosides, cephalosporins, quinolones, penicillins, sulfonamides, ketoconazole, miconazole, acyclovir, ganciclovir, azidothymidine, vitamins, interferon; anticonvulsants such as phenytoin and valproic acid; antidepressants such as amitriptyline and trazodone; antiparkinsonism drugs; cardiovascular agents such as calcium channel blockers, antiarythmics, beta blockers; antineoplastics such as cisplatin and methotrexate, corticosteroids such as dexamethasone, hydrocortisone, prednisolone, and triamcinolone; NSAIDs such as ibuprofen, salicylates indomethacin, piroxicam; hormones such as progesterone, estrogen, testosterone; growth factors; carbonic anhydrase inhibitors such as acetazolamide; prostaglandins; antiangiogenic agents; neuroprotectants; neurotrophins; growth factors; cytokines; chemokines; cells such as stem cells, primary cells, and genetically engineered cells; tissues; and other agents known to those skilled in the art.

Referring to FIG. 1, a cross-section view of a structure in accordance with the present disclosure is illustrated. The structure includes an ePTFE layer 1 and an espin layer 2. Such a configuration may be processed as a component to be used in the construction of a graft or stent-graft assembly depending on the geometrical shape and properties desired. It may also be used as a covering for other medical devices including but not limited to occlusion devices, defect closure devices, cellular encapsulation devices, regenerative medicine scaffolds, cosmetic implants, cardiovascular patches and abdominal patches as examples. However, this list is not all inclusive and many other applications are contemplated in accordance with the present disclosure.

The inner (blood contacting) and outer (tissue contacting) layers of the present disclosure may have different porosities to enhance or inhibit, respectively, cellular ingrowth or attachment. Applications for the implantable electrostatically spun vascular prosthesis would include but not be limited to artificial by-pass graft, coronary artery by-pass graft, by-pass shunt, hemodialysis, arteriovenous graft, homograft, pulmonary allograft, or pulmonary shunt. This tubular structure can include characteristics of enhanced radial tensile strength, suture hole tearing resistance and enhanced axial tear resistance.

Figure 2:
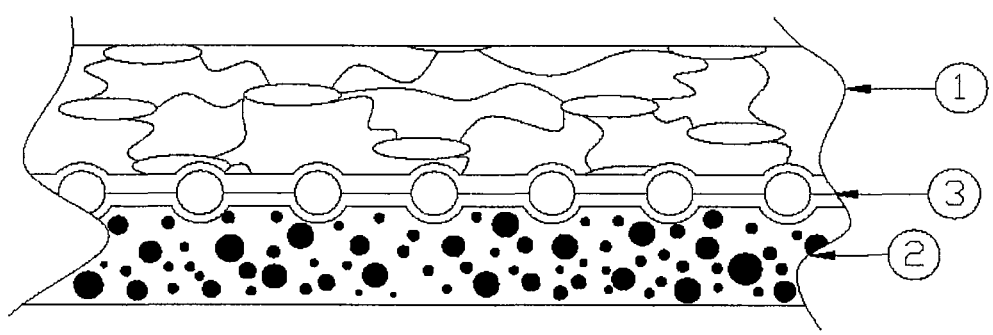

Referring to FIG. 2, a cross-section view of a device in accordance with the present disclosure is illustrated. The device includes an ePTFE layer 1, a frame 3 (such as a stent frame), and an espin layer 2. Such a configuration may be used in an application where it is desirable to bond ePTFE to a formed structure such as a stent, occlusion device or other frame. The espin layer provides adhesion while also providing a substantially different pore size and structure on the luminal or abluminal surface depending on the application. In such a configuration, the espin layer can be applied directly to the surface of the frame or added as a preformed sheet that is combined with the ePTFE and frame as part of the sintering or curing process. In general, such a configuration could be utilized in any application where the encapsulation of a support frame is desirable. For instance, such a configuration could be used in connection with a conventional stent.

Various stent types and stent constructions may be employed in the present disclosure. Among the various stents useful include, without limitation, self-expanding stents and balloon expandable extents. The stents may be capable of radially contracting, as well. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials contemplated by the present disclosure include, but are not limited to, stainless steel, platinum, gold, titanium and other biocompatible metals, as well as polymeric stents.

The configuration of the stent may also be chosen from any suitable geometry as would be known in the art. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like.

Turning to FIG. 3, a cross-section view of another configuration is illustrated. The configuration includes an ePTFE layer 1, an espin layer 2, and another ePTFE layer 1, such to that the espin layer 2 is sandwiched between the ePTFE layers 1. Such a construction allows the user to manipulate the mechanical properties of the composite as desired, for example improving material recovery after compression. The espin material selection can be adjusted to improve bonding properties between layers and the espin layer can be used to inhibit cellular proliferation through the middle on the construction. In this instance, it may be advantageous to allow cells to migrate and proliferate from both sides (luminal and abluminal in the case of a graft) but communication between the two may not be desired. The middle espin layer can be designed with a porosity that will inhibit this cellular communication.

Turning to FIG. 4, a cross-section of yet another configuration in accordance with the present disclosure is illustrated. The device includes an ePTFE layer 1, an espin layer 2, a frame 3, and another ePTFE layer 1. In this manner, the frame increases the radial strength of the overall construction and also promotes recovery during deployment of the construction. For instance, in certain embodiments of the present disclosure, the frame is a stent. The stent frame provides a structural backbone within the structure, which prevents suture wall tear out.

The electro-spun layer is preferably applied directly to the frame through electrospinning methods understood by those skilled in the art; however, it could also be applied by lamination as well. The technique involves pressing an espun layer onto a second material layer and heating to a complimentary temperature. In all configurations, the design can include or exclude a structural frame. These frames can take the form of stents, occlusion coils or frames, regenerative medicine scaffolds, structural reinforcements, pacing or monitoring leads, tissue anchors or tacks, biological stimulation devices, biomimetic implants, signal receivers or transmitters, orthopedic fixation devices or any other metallic, polymeric, ceramic or other therapeutic device.

The properties and characteristics of the composite material are a compilation of the frame, espun, and ePTFE membrane layers. The composite can be prepared with controlled fiber, node, and fibril sizes and manipulated mechanically, such as to improve bond strength, elongation properties, and tensile strengths, in the final composite.

Typical construction of multiple layers may produce thickness ranging from about 0.0001 inches to about 0.25 inches overall thicknesses at widths of about 0.032 inches to about 80 inches. The individual layers can have a thickness that varies from about 0.0001 inches to about 0.25 inches. Final material size varies greatly as the composites can be produced as sheets or tubes at continuous roll lengths. The composite internodal distance (IND) can be about 0.1 to about 200 µm with porosity ranging from about 20 to 90%. Pore structure as defined by ASTM F316, incorporated by reference herein, can range from about 0.05 to about 50 µm. Due to the construction of the composites, the IND, pore size and porosity can vary from layer to layer, within the cross section of the composite, depending on the construction. An example would be an asymmetrical construction where pores change in size from large to small based on layer evaluations from surface to surface throughout the media.

The materials used in the construction of frame and graft structures as described herein, may be produced as an assembly using prefabricated components, from materials described herein. The materials may be assembled in individual layers or in bi-layers. It may be beneficial to produce a construction as illustrated in FIG. 2 as a component, to be used in another construction described herein. For the embodiment illustrated in FIG. 4, prefabricated components can be coupled with the final frame and additional layers of ePTFE as desired to produce the finalized assembly.

For instance, in embodiments in which the electrospun layer is part of a tubular structure, as previously described herein, the diameter of fibers in the espin layer can range from about 10 nm to 2000 nm in size, wall thicknesses ranging from about 75µ to 1.5 mm, and average inside diameter ranging from about 0.2 mm to 50 mm.

The devices of the present disclosure can be prepared with controlled fiber, node and fibril sizes and manipulated mechanical values such as bond strength, elongation properties and tensile strengths.

Expanded PTFE is comprised of a microstructure consisting of solid nodes interconnected by fine, highly oriented fibrils. The expanded PTFE nodes and fibrils provide unique biocompatible porous structures. The microstructure of the material can be adjusted to provide a matrix for cellular attachment and in-growth. The expanded PTFE and electrospun PTFE microstructures are designed to enhance, inhibit or retard the migration of endothelium during the early phase of healing.

As an example, an ePTFE microstructures which have a node to fibril distance of about 10~20 µm permit very little transmural cellular in-growth. Optimal porosity for cellular in growth ranges between 20 and 80 µm. Studies have shown porosity of >120 µm have been associated with reduced in growth and poor Neointima adhesion based on the smaller surface are available for cellular adhesion and locomotion.

In certain embodiments of the present disclosure, the process can require a dispersion or suspension of PTFE solids between about 10 to 85% by weight to aid in the processing of the collected fibrous mat into a form that has sufficient green strength. However, as described above, other suitable polymers can be utilized for the espin dispersion. If the solid content in the dispersion is too low, there will be no, or poor, mechanical integrity to the resulting material. Second, the selection of the polymer used to increase the viscosity of the solution, suspension or dispersion to be spun must be selected carefully.

Additionally, when sintering or bonding espin layers it is necessary to insure that temperatures are selected to properly sinter the material, such that the resulting product has good mechanical integrity.

To produce a non-woven espin PTFE material, a narrow particle size distribution PTFE powder is provided in an aqueous dispersion. The particle size would preferably be about 0.05 to 0.8µ. About 1 to 10 wt % by weight of a fiberizing polymer is added to the volume of PTFE aqueous dispersion. The fiberizing polymer should have a high solubility in water with a solubility of greater than about 0.5 wt % being preferred. It is preferable that the fiberizing polymer has an ash content of less than about 5 wt %, when sintered at about 400° C., with even lower being more preferred. Without limit thereto, particularly preferred fiberizing polymers can include dextran, alginates, chitosan, guar gum compounds, starch, polyvinylpyridine compounds, cellulosic compounds, cellulose ether, hydrolyzed polyacrylamides, polyacrylates, polycarboxylates, polyvinyl alcohol, polyethylene oxide, polyethylene glycol, polyethylene imine, polyvinylpyrrolodone, polylactic acid, polymethacrylic acid polyitaconic acid, poly 2-hydroxyelthyl acrylate, poly 2-dimethylaminoethyl methacrylate-co-acrylamide, poly n-isopropylacrylamde, poly 2-acrylamido-2-methyl-1-propanesulfonic acid, poly (methoxyethylene), poly(vinyl alcohol), poly(vinyl alcohol)

12% acetyl, poly(2,4-dimethyl-6-triazinylethylene), poly(3-morpholinylethylene), poly(N-1,2,4-triazolyethylene), poly(vinyl sulfoxide), poly(vinyl amine), poly(N-vinyl pyrrolidone-co-vinyl acetate), poly(g-glutamic acid), poly(N-propanoyliminoethylene), poly(4-amino-sulfo-aniline), poly[N-(p-sulphophenyl)amino-3-hydroxymethyl-1,4-phenyleneimino-1,4-phenylene)], isopropyl cellulose, hydroxyethyl, hydroxylpropyl cellulose, cellulose acetate, cellulose nitrate, alginic ammonium salts, i-carrageenan, N-[(3'-hydroxy-2',3'-dicarboxy)ethyl]chitosan, konjac glocomannan, pullulan, xanthan gum, poly(allyammonium chloride), poly(allyammonium phosphate), poly(diallydimethylammonium chloride), poly(benzyltrimethylammonium chloride), poly(dimethyldodecyl(2-acrylamidoethyly)ammonium bromide), poly(4-N-butylpyridiniumethylene iodine), poly(2-N-methylpridiniummethylene iodine), poly(N methylpryidinium-2,5-diylethenylene), polyethylene glycol polymers and copolymers, cellulose ethyl ether, cellulose ethyl hydroxyethyl ether, cellulose methyl hydroxyethyl ether, poly(1-glycerol methacrylate), poly(2-ethyl-2-oxazoline), poly(2-hydroxyethyl methacrylate/methacrylic acid) 90:10, poly(2-hydroxypropyl methacrylate), poly(2-methacryloxyethyltrimethylammonium bromide), poly(-vinyl-1-methylpyridinium bromide), poly(2-vinylpyridine N-oxide), poly(2-vinylpyridine), poly(3-chloro-2-hydroxypropyl-2-methacryloxyethyldimethylammonium chloride), poly(4-vinylpyridine N-oxide), poly(4-vinylpyridine), poly(acrylamide/2-methacryloxyethyltrimethylammonium bromide) 80:20, poly(acrylamide/acrylic acid), poly(allylamine hydrochloride), poly(butadiene/maleic acid), poly(diallyldimethylammonium chloride), poly(ethyl acrylate/acrylic acid), poly(ethylene glycol)bis(2-aminoethyl), poly(ethylene glycol) monomethyl ether, poly(ethylene glycol)-bisphenol A diglycidyl ether adduct, poly(ethylene oxide-b-propylene oxide), poly(ethylene/acrylic acid) 92:8, poly(l-lysine hydrobromide), poly(1-lysine hydrobromide), poly(maleic acid), poly(n-butyl acrylate/2-methacryloxyethyltrimethylammonium bromide), poly(N-iso-propylacrylamide), poly(N-vinylpyrrolidone/2-dimethylaminoethyl methacrylate), dimethyl sulfatequaternary, poly(N-vinylpyrrolidone/vinyl acetate), poly(oxyethylene) sorbitan monolaurate (Tween 20®), poly(styrenesulfonic acid), poly(vinyl alcohol), N-methyl-4(4'-formylstyryl)pyridinium, methosulfate acetal, poly(vinyl methyl ether), poly(vinylamine) hydrochloride, poly(vinylphosphonic acid), poly(vinylsulfonic acid) sodium salt, polyaniline, and combinations thereof. Again, however, such fiberizing polymers are also contemplated for use with other polymer espin dispersions.

A particularly preferred fiberizing polymer is polyethylene oxide with a molecular weight between about 50,000 to 4,000,000 amu polyethyleneoxide. After mixing, the PTFE and fiberizing polymer dispersion is preferably allowed to homogenize. In a particularly preferred method the polymer solution is allowed to form slowly, without agitation, followed by transfer to a jar roller that will turn it at a constant rate for several more days. The present disclosure contemplates the use of dispersions of greater than 50,000 cPs to provide for more uniform and consistent fiber formation as well as faster builds. It is preferred to create a uniform solution that has little to no air trapped in the resulting highly viscous mixture. Once the dispersion is of uniform consistency it is preferably filtered to remove any clumps or gels. The filtered dispersion with the desired viscosity is then loaded, in a controlled pumping device with a fixed conductive element which acts as the charge source.

A particularly preferred conductive element is one with one or several orifices. The orifice size is preferably, but not limited to, about 0.01 to 3.0 mm in diameter. The ejection volume from the pumping device is set to a predetermined rate that is dependent on the form being made and the desired fiber diameters. The charge source is preferably connected to the positive side of a precision DC power supply. The negative side of the power supply is preferably connected to the collection surface or target. The polarity can be reversed but this is not preferred.

The surface can be a drum, device or sheet. The surface can be a metal, ceramic or polymeric material with particularly preferred materials selected from stainless steel, cobalt chrome, nickel titanium (nitinol) and magnesium alloys. The voltage on the power supply is increased to the desired voltage to uniformly draw out the polymer/PTFE solution.

The applied voltage is typically from about 2,000 to 80,000 volts. The charge induced by the connection of the power supply repels the charged polymer away from the charge source and attracts them to the collection surface.

The collection target is preferably placed perpendicular to the pump and orifice system and is moved in at least one direction such that the entire surface is uniformly covered, with the fibers drawn towards the target. Once the collection surface has been adequately covered the material is preferably cured, sintered, and dried (which can occur simultaneously or in a series of steps), either in place, by placing the entire collection surface in an oven, or by removing the sheet tube or other form from the collection surface and sintering it in an oven.

It is well known to those skilled in the art that espin fabrics undergo shrinkage upon sintering. While not limited to any theory the shrinkage is believe to occur in two steps. Initially, the fibers and fabrics as spun contain both water and a fiberizing polymer as previously described. Upon completion of spinning the samples dry and undergo a small degree of fiber rearrangement. At a later time the samples are heated by exposing the fibers and fabrics to temperatures of about 35° C. to about 485° C. for a period of time.

To accommodate for shrinkage, the fiber and fabrics can be spun onto an expanded structure. The structure can then be removed or contracted. During sintering of the espin layer, the fabric shrinks to a smaller size without cracking. Another method involves spinning the fibers and fabrics onto a structure which can then be expanded and/or contracted prior to or during sintering. The range of contraction or expansion and contraction is on the order of about 3 to 100% and depends upon the thickness and size of the electrodeposited fabric. Alternatively the espin layer can be placed upon a surface which also contracts during sintering.

For a sheet of fabric, if the direction of the deposition is given as the perpendicular to the plane of the fabric then contraction or expansion/contraction must occur in at least one or more of the directions in the plane of the fabric. For a fabric deposited upon a cylindrical surface the fabric must be contracted or contracted/expanded radially and/or longitudinally. For a spherical surface the fabric must be contracted or contracted/expanded radially. These basic concepts of contraction and/or expansion/contraction can be applied to any electrospun fabric independent to the shape of the surface upon which it was spun. Thus, very complex fabric shapes based upon espin fabric become possible.

The espin layer is preferably fibrous. Particularly preferred espin fibers have a diameter of at least 0.1μ. In a particularly preferred embodiment the product, after sintering, has fibers deposited in a density such there is a range of distances of 0.1 to 50μ between points of contact.

The present disclosure can be better understood with reference to the following examples.

EXAMPLES

The following general guidelines are used for the processing examples described herein of various ePTFE and espin composite constructions.

1. In espin PTFE embodiments, the viscosity of the dispersion may be changed by the addition or removal of water from the dispersion without changing the PEQ to PTFE ratio.

2. A radially expanded ePTFE tube or biaxial oriented sheet is placed over a round or flat base plate to form a desired geometric shape.

3. The espin polymer layer is applied at a desired thickness, typically about 0.5 to 1000μm, onto the ePTFE or onto a surface which is then mated to the ePTFE membrane, resulting in a composite structure.

4. If the espin coating is applied wet to the ePTFE, it is allowed to dry before moving to the next process. However, if it is processed as a single espin sheet and has dried, it will be mated to the oriented porous ePTFE layer. The mating process between the materials can be repeated multiple times until a desired multilayered composite structure is created.

5. The ePTFE/espin composite is then covered with a non-sticking release foil.

6. Once the composite is positioned against a base tool, pressure is applied to the surface of the foil, thereby aiding the bonding process.

7. The composite construction is placed in an oven at temperatures of about 35° C. to about 485° C. to allow all materials to bond together. The bonding temperature selection is based on material selection.

8. Once the part is removed from the oven and cooled at a rate of about 15 to 25 degrees per minute, it is uncovered and tested for specified properties.

Example 1

Type I Construction: ePTFE/espun PTFE

A biaxially (Biax) expanded approximately 10 cm long ePTFE tube with an intermodal distance (ND) of 20μ, internal diameter (ID) of 4 mm, wall thickness (WT) of 0.1 mm, and porosity of 77.27% was placed over and centered along a 4 mm exterior diameter (OD) stainless steel (SS) tube of 35 cm length. The tube assembly was placed into a rotating chuck such that it was positioned to allow espinning along the entire length of the turning tube assembly.

An approximately 85,900 cPs espinning dispersion based on a mixture of 4.2% (PEO/PTFE), 300,000 amu polyethylene oxide and Daikin D210 60% PTFE dispersion which had been allowed to homogenize and then turned and filtered to achieve a smooth consistency was placed into a 10 ml plastic syringe fitted with a 22 gauge needle. The syringe was placed into a Harvard Model 702100 syringe pump and set to 2.0 ml/hour pumping rate. The needle tip was positioned at approximately 9.5 cm from the rotating tube assembly. The rotation of the tube assembly was approximately 60 rpm. A traverse was used to move the espinning needle along the length of the tube with a rate of travel of 3.2 mm/sec. The return points for the traverse were set at the ends of the Biax tube. A voltage of 9.2 kV was employed. PTFE was espun onto the tube for 30 minutes under these conditions to yield an approximately 25μ (as deposited post sintering) thick covering of PTFE fibers.

After allowing the Biax tube/espun PTFE assembly to dry excess espun PTFE was removed and the composite graft was sintered on the SS tube for 10 minutes at 385° C. After cooling, isopropanol was used to facilitate the removal of the composite graft from the tube.

Example 2

Type I Construction: ePTFE/espun PTFE

Same as Example 1 except: After drying and removal of excess PTFE the tube assembly was then wrapped in 80μ stainless steel (SS) foil followed by being further wrapped with unsintered 25μ thick ePTFE membrane applied around the entire assembly. The tube assembly was then placed in an oven preheated to 385° C. for 15.0 minutes. Upon removal from the oven and cooling the SS foil and 25μ thick membrane were removed to reveal the composite graft. Isopropanol was used to facilitate the removal of the graft from the tube.

Example 3

Type II Construction: ePTFE/stent/espun PTFE

A biaxially (Biax) expanded approximately 6 cm long ePTFE tube with an intermodal distance (IND) of 20μ, internal diameter (ID) of 4 mm, wall thickness (WT) of 0.1 mm, and porosity of 77.27% was placed over and at the end of a 4 mm exterior diameter (OD) stainless steel tube of 35 cm length. A generic stent 5.2 cm long, 4.25 mm ID, and a WT of 0.125 mm was then expanded slightly, placed, and centered over the ePTFE tube. The ePTFE tube assembly was then positioned at the midpoint of the SS tube and placed into a rotating chuck such that it was positioned to allow espinning along the entire length of the turning tube assembly.

An approximately 85,900 cPs espinning dispersion based on a mixture of 4.2% (PEO/PTFE), 300,000 amu polyethylene oxide and Daikin D210 60% PTFE dispersion which had been allowed to homogenize and then turned and filtered to achieve a smooth consistency was placed into a 10 ml plastic syringe fitted with a 22 gauge needle. The syringe was placed into a Harvard Model 702100 syringe pump and set to a 2.0 ml/hour pumping rate. The needle tip was positioned at approximately 9.5 cm from the rotating stent/tube assembly. The rotation of the stent/tube assembly was approximately 60 rpm. A traverse was used to move the espinning needle along the length of the SS tube with a rate of travel of 3.2 mm/sec. The return points for the traverse were set at the ends of the Biax tube. A voltage of 9.2 kV was employed. PTFE was espun onto the tube for 60 minutes under these conditions to yield an approximately 50μ (as deposited post sintering) thick covering of PTFE fibers.

After allowing the tube assembly to dry the composite stent-graft was sintered on the SS tube for 15 minutes at 385° C. After cooling, isopropanol was used to facilitate the removal of the stent-graft from the tube.

Example 4

Type II Construction: ePTFE/stent/espun PTFE

Same as Example 3 except: After allowing the stent-tube assembly to dry it was then wrapped in 80μ stainless steel (SS) foil followed by being further wrapped with unsintered 25μ thick ePTFE membrane applied around the entire assembly. The stent-tube assembly was then placed in an oven preheated to 385° C. for 15.0 minutes. Upon cooling the SS foil and 25µ thick membrane were removed to reveal the stent-graft. Isopropanol was used to facilitate the removal of the graft from the tube.

Example 5

Type III Construction: ePTFE/espun PTFE/ePTFE

A biaxially (Biax) expanded approximately 10 cm long ePTFE tube with an intermodal distance (IND) of 20µ, internal diameter (ID) of 4 mm, wall thickness (WT) of 0.1 mm, and porosity of 77.27% was placed over and centered along a 4 mm exterior diameter (OD) stainless steel of 35 cm length. The tube assembly was placed into a rotating chuck such that it was positioned to allow espinning along the entire length of the turning tube assembly.

An approximately 85,900 cPs espinning dispersion based on a mixture of 4.2% (PEO/PTFE), 300,000 amu polyethylene oxide and Daikin D210 60% PTFE dispersion which had been allowed to homogenize and then turned and filtered to achieve a smooth consistency was placed into a 10 ml plastic syringe fitted with a 22 gauge needle. The syringe was placed into a Harvard Model 702100 syringe pump and set to a 2.0 ml/hour pumping rate. The needle tip was positioned at approximately 9.5 cm from the rotating tube assembly. The rotation of the tube assembly was approximately 60 rpm. A traverse was used to move the espinning needle along the length of the tube with a rate of travel of 3.2 mm/sec. The return points for the traverse were set at the ends of the Biax tube. A voltage of 9.2 kV was employed. PTFE was espun onto the tube for 60 minutes under these conditions to yield an approximately 50µ (as deposited post sintering) thick covering of PTFE fibers.

After allowing the tube assembly to dry at 50° C. for one hour an ePTFE membrane of basis weight 9.955 gsm and thickness of 28µ was wrapped 4 times around the tube assembly. The tube assembly was then wrapped with unsintered 25µ thick ePTFE membrane applied tightly around the entire assembly. The tube assembly was then placed into an oven preheated to 385° C. for 15.0 minutes. After cooling the 25µ thick membrane was removed to reveal the graft. Isopropanol was used to facilitate the removal of the graft from the tube.

Example 6

Type III Construction: ePTFE/espun PTFE/ePTFE

Same as Example 5 except: After allowing the tube assembly to dry an ePTFE membrane of basis weight 9.955 gsm and thickness of 28µ was wrapped 4 times around the tube assembly. The tube assembly was then wrapped in 80µ stainless steel (SS) foil followed by being further wrapped with unsintered 25µ thick ePTFE membrane applied around the entire assembly. The tube assembly was then placed in an oven preheated to 385° C. for 15.0 minutes. Upon cooling the SS foil and 25µ thick membrane were removed to reveal the graft. Isopropanol was used to facilitate the removal of the graft from the tube.

Example 7

Type IV Construction: ePTFE/stent/espun PTFE/ePTFE

A biaxially (Biax) expanded approximately 6 cm long ePTFE tube with an intermodal distance (IND) of 20µ, internal diameter (ID) of 4 mm, wall thickness (WT) of 0.1 mm, and porosity of 77.27% was placed over and at the end of a 4 mm exterior diameter (OD) stainless steel of 35 cm length. A generic stent 5.2 cm long, 4.25 mm ID, and a WT of 0.125 mm was then expanded slightly, placed, and centered over the ePTFE tube. The ePTFE tube assembly was then positioned at the midpoint of the SS tube and placed into a rotating chuck such that it was positioned to allow espinning along the entire length of the turning tube assembly.

An approximately 85,900 cPs espinning dispersion based on a mixture of 4.2% (PEO/PTFE), 300,000 amu polyethylene oxide and Daikin D210 60% PTFE dispersion which had been allowed to homogenize and then turned and filtered to achieve a smooth consistency was placed into a 10 ml plastic syringe fitted with a 22 gauge needle. The syringe was placed into a Harvard Model 702100 syringe pump and set to a 2.0 ml/hour pumping rate. The needle tip was positioned at approximately 9.5 cm from the rotating stent/tube assembly. The rotation of the stent/tube assembly was approximately 60 rpm. A traverse was used to move the espinning needle along the length of the rod with a rate of travel of 3.2 mm/sec. The return points for the traverse were set at the ends of the stent. A voltage of 9.2 kV was employed. PTFE was espun onto the tube for 60 minutes under these conditions to yield an approximately 50µ (as deposited post sintering) thick covering of PTFE fibers.

After allowing the tube assembly to dry an ePTFE membrane of basis weight 9.955 gsm and thickness of 28µ was wrapped 4 times around the stent/tube assembly. The stent/tube assembly was then wrapped with unsintered 25µ thick ePTFE membrane applied tightly around the entire assembly. The tube assembly was then placed into an oven preheated to 385° C. for 15.0 minutes. After cooling the 25µ thick membrane was removed to reveal the stent-graft. Isopropanol was used to facilitate the removal of the stent-graft from the tube.

Example 8

Type IV Construction: ePTFE/stent/espun PTFE/ePTFE

Same as Example 7 except: After allowing the tube assembly to dry an ePTFE membrane of basis weight 9.955 gsm and thickness of 28µ was wrapped 4 times around the stent-tube assembly. The stent-tube assembly was then wrapped in 80µ stainless steel (SS) foil followed by being further wrapped 5 times with unsintered 25µ thick ePTFE membrane applied around the entire assembly. The tube assembly was then placed in an oven preheated to 385° C. for 15.0 minutes. Upon cooling the SS foil and 25µ thick membrane were removed to reveal the stent-graft. Isopropanol was used to facilitate the removal of the graft from the tube.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in-whole or in-part. Furthermore, those of ordinary skill in the art will appreciate that the foregoing description is by way of example only, and is not intended to limit the disclosure.

What is claimed is:

1. A composite structure comprising a tubular frame and comprising a tubular polymeric inner surface and a tubular polymeric outer surface, wherein at least one of the tubular polymeric inner surface and tubular polymeric outer surface comprises a plurality of electrospun poly(tetrafluoroethylene) (PTFE) nanofibers, and wherein the PTFE nanofibers have a density such that there is a range of distances of about 0.1μ to about 50μ between points of contact of the nanofibers.

2. The composite structure of claim 1, wherein both the tubular polymeric inner surface and tubular polymeric outer surface comprise a plurality of electrospun PTFE nanofibers.

3. The composite structure of claim 1, further comprising one or more additional layers of polymeric material.

4. The composite structure of claim 3, wherein the one or more additional layers of polymeric material comprises a second plurality of electrospun poly(tetrafluoroethylene) (PTFE) nanofibers.

5. The composite structure of claim 3, wherein the one or more additional layers of polymeric material comprises nylon, polyurethane, polyester, fluorinated ethylene propylene, or a combination thereof in the form of electrospun fibers.

6. The composite structure of claim 3, wherein at least one of the tubular polymeric inner surface, the tubular polymeric outer surface, and the one or more additional layers of polymeric materials comprises expanded PTFE.

7. The composite structure of claim 3, wherein the one or more additional layers of polymeric material comprises a thermoplastic or elastic material.

8. The composite structure of claim 1, wherein one of the tubular polymeric inner surface and tubular polymeric outer surface comprises nylon, polyurethane, polyester, fluorinated ethylene propylene, or a combination thereof in the form of electrospun fibers.

9. The composite structure of claim 1, wherein the tubular polymeric inner surface and a tubular polymeric outer surface have different pore sizes.

10. The composite structure of claim 1, wherein the tubular frame comprises a metal.

11. The composite structure of claim 1, wherein the tubular frame comprises stainless steel, platinum, gold, titanium, polymer, or nitinol.

12. The composite structure of claim 1, wherein the tubular frame comprises a stent.

13. The composite structure of claim 1, further comprising a bioactive agent.

14. The composite structure of claim 13, wherein the bioactive agent is selected from the group consisting of antibiotics, antifungals, antivirals, anticonvulsants, antidepressants, antiparkinsonism drugs, cardiovascular agents, antineoplastics, corticosteroids, NSAIDs, hormones, growth factors, carbonic anhydrase inhibitors, prostaglandins, antiangiogenic agents, neuroprotectants, neurotrophins, growth factors, cytokines, chemokines, cells, tissues, and combinations thereof.

15. The composite structure of claim 1, wherein each of the inner surface and outer surface comprise at least one electrospun layer of a plurality of electrospun PTFE nanofibers.

16. The composite structure of claim 15, wherein the pore structure of one or more of the electrospun layers as defined by ASTM F316 is between about 0.05 μm and about 50 μm.

17. The composite structure of claim 15, wherein one or more of the electrospun layers has a porosity to enhance cellular ingrowth or attachment.

18. The composite structure of claim 15, wherein one or more of the electrospun layers has a porosity to inhibit cellular ingrowth or attachment.

19. The composite structure of claim 1, wherein the composite structure is comprised primarily of micron and submicron sized electrostatically spun PTFE fibers in random orientation on the frame.

20. The composite structure of claim 1, wherein the tubular polymeric inner surface comprises a plurality of electrospun poly(tetrafluoroethylene) (PTFE) nanofibers.

21. A composite structure comprising a tubular frame and comprising at least three tubular polymeric layers associated therewith, wherein one tubular polymeric layer is positioned to form the inner surface of the composite structure and one tubular polymeric layer is positioned to form the outer surface of the composite structure, wherein at least one of the three tubular polymeric layers comprises a plurality of electrospun poly(tetrafluoroethylene) (PTFE) nanofibers, and wherein the nanofibers have a density such that there is a range of distances of about 0.1μ to about 50μ between points of contact of the nanofibers.

22. The composite structure of claim 21, wherein at least two of the tubular polymeric layers comprise a plurality of electrospun PTFE nanofibers.

23. The composite structure of claim 21, wherein at least one of the three tubular polymeric layers is positioned to form the inner surface of the composite structure and the one tubular polymeric layer positioned to form the outer surface of the composite structure comprises a plurality of electrospun PTFE nanofibers.

24. The composite structure of claim 21, wherein at least one of the tubular polymeric layers comprises nylon, polyurethane, polyester, fluorinated ethylene propylene, or a combination thereof in the form of electrospun fibers.

25. The composite structure of claim 21, wherein at least one of the tubular polymeric layer positioned to form the inner surface of the composite structure and the tubular polymeric layer positioned to form the outer surface of the composite structure comprises nylon, polyurethane, polyester, fluorinated ethylene propylene, or a combination thereof in the form of electrospun fibers.

26. The composite structure of claim 21, wherein the tubular polymeric layer positioned to form the inner surface of the composite structure and the tubular polymeric layer positioned to form the outer surface of the composite structure have different pore sizes.

27. The composite structure of claim 21, wherein the tubular frame comprises a metal.

28. The composite structure of claim 21, wherein the tubular frame comprises stainless steel, platinum, gold, titanium, polymer, or nitinol.

29. The composite structure of claim 21, wherein the tubular frame comprises a stent.

30. The structure of claim 21, further comprising a bioactive agent.

31. The structure of claim 30, wherein the bioactive agent is selected from the group consisting of antibiotics, antifungals, antivirals, anticonvulsants, antidepressants, antiparkinsonism drugs, cardiovascular agents, antineoplastics, corticosteroids, NSAIDs, hormones, growth factors, carbonic anhydrase inhibitors, prostaglandins, antiangiogenic agents, neuroprotectants, neurotrophins, growth factors, cytokines, chemokines, cells, tissues, and combinations thereof.

32. The composite structure of claim 21, wherein each of the inner surface and outer surface comprise at least one electrospun layer of a plurality of electrospun PTFE nanofibers.

33. The composite structure of claim 32, wherein the pore structure of one or more of the electrospun layers as defined by ASTM F316 is between about 0.05 μm and about 50 μm.

34. The composite structure of claim 32, wherein one or more of the electrospun layers has a porosity to enhance cellular ingrowth or attachment.

35. The composite structure of claim 32, wherein one or more of the electrospun layers has a porosity to inhibit cellular ingrowth or attachment.

36. The composite structure of claim 21, wherein the composite structure is comprised primarily of micron and submicron sized electrostatically spun PTFE in random orientation on the frame.

37. The composite structure of claim 21, wherein the tubular polymeric layer positioned to form the inner surface comprises a plurality of electrospun poly(tetrafluoroethylene) (PTFE) nanofibers.

* * * * *